(12) United States Patent
Maeno et al.

(10) Patent No.: US 8,551,332 B2
(45) Date of Patent: Oct. 8, 2013

(54) AFFINITY PARTICLE AND AFFINITY SEPARATION METHOD

(75) Inventors: Katsuyuki Maeno, Yokohama (JP); Kazuyuki Miyazawa, Yokohama (JP); Akira Ishikubo, Yokohama (JP); Kazuhiko Ishihara, Yokohama (JP)

(73) Assignees: Shiseido Company, Ltd., Tokyo (JP); Kazuhiko Ishihara, Mitaka (JP)

( * ) Notice: Subject to any disclaimer, the term of this patent is extended or adjusted under 35 U.S.C. 154(b) by 1093 days.

(21) Appl. No.: 12/495,936

(22) Filed: Jul. 1, 2009

(65) Prior Publication Data

US 2010/0137133 A1    Jun. 3, 2010

Related U.S. Application Data

(63) Continuation of application No. 11/580,000, filed as application No. PCT/JP2005/009088 on May 18, 2005, now abandoned.

(30) Foreign Application Priority Data

May 24, 2004   (JP) ................................. 2004-153253
May 11, 2005   (JP) ................................. 2005-138560

(51) Int. Cl.
*B01D 15/08*   (2006.01)

(52) U.S. Cl.
USPC ..................... 210/198.2; 210/502.1; 210/635; 210/656

(58) Field of Classification Search
USPC ............ 210/635, 656, 198.2, 502.1; 502/401
See application file for complete search history.

(56) References Cited

U.S. PATENT DOCUMENTS

| | | | | |
|---|---|---|---|---|
| 4,298,500 A | * | 11/1981 | Abbott | .............................. 502/7 |
| 4,767,670 A | * | 8/1988 | Cox et al. | ...................... 428/403 |
| 5,045,190 A | * | 9/1991 | Carbonell et al. | ......... 210/198.2 |
| 5,137,627 A | * | 8/1992 | Feibush | .................... 210/198.2 |
| 5,141,806 A | * | 8/1992 | Koontz | .................... 428/315.5 |
| 5,277,813 A | * | 1/1994 | Feibush et al. | ............. 210/502.1 |
| 5,374,755 A | * | 12/1994 | Neue et al. | .................... 556/400 |

(Continued)

FOREIGN PATENT DOCUMENTS

JP    59-169532    *   9/1984

OTHER PUBLICATIONS

U.S. Patent and Trademark Translation No. PTO 08-4047 of Yamawaki (Japan Patent No. 59-169,532).*

(Continued)

*Primary Examiner* — Ernest G Therkorn

(57) ABSTRACT

The present invention is affinity particles that are characterized by having phosphorylcholine groups represented by the following formula (1) covalently bonded onto the surface of inorganic powder and also by having ligands having specific affinity with a certain target substance covalently bonded or adsorbed onto the surface of inorganic powder.

The object of the present invention is to provide an affinity separation method that uses affinity particles utilizing inexpensive inorganic particles and is capable of separating the target substance easily and with high accuracy.

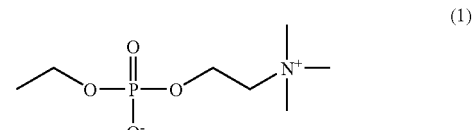

(1)

4 Claims, 8 Drawing Sheets

(56) References Cited

U.S. PATENT DOCUMENTS

| | | | |
|---|---|---|---|
| 5,431,807 A * | 7/1995 | Frechet et al. | 210/198.2 |
| 5,438,000 A * | 8/1995 | Legario et al. | 436/17 |
| 6,884,345 B1 * | 4/2005 | Irgum et al. | 210/198.2 |
| 7,125,488 B2 * | 10/2006 | Li | 210/198.2 |
| 7,560,023 B2 * | 7/2009 | Miyazawa et al. | 210/198.2 |
| 2002/0005380 A1 * | 1/2002 | Sato et al. | 210/616 |
| 2006/0060533 A1 * | 3/2006 | Miyazawa et al. | 210/656 |

OTHER PUBLICATIONS

U.S. Patent and Trademark Translation No. PTO 08-2201 of Ishihara (Japan Patent No. 2002-98676).*

* cited by examiner

AFFINITY PARTICLE AND AFFINITY SEPARATION METHOD

CROSS REFERENCE TO A RELATED APPLICATIONS

This is a continuation patent application of application Ser. No. 11/580,000, filed Nov. 9, 2006, now abandoned, which, in turn, is a 371 of PCT/JP2005/009088, filed May 18, 2005.

TECHNICAL FIELD

The present invention relates to affinity particles and an affinity separation method. More specifically, it relates to affinity particles utilizing inorganic particles and an affinity separation method that allows easy and highly precise separation of the target substance. The present invention is very useful in various separation, purification, and testing methods including latex agglutination methods and immunoprecipitation methods that allow easy and highly sensitive detection of the target substance.

BACKGROUND ART

Conventionally, column chromatography has been used for separation and purification of biological substances. However, column separation has some fatal problems as described in the following (1) to (3):
(1) Many kinds of columns have to be used to obtain the target substance, resulting in a poor purification efficiency.
(2) A verification test is required to make sure the target substance is contained in the fractionated ingredients, which means purification is time consuming.
(3) Because of the large purification loss, a large quantity of the sample is required.

On the other hand, for separation and purification of the target substances, affinity particles and affinity columns supporting ligands are used (Patent Document 1 and Patent Document 2).

However, separation and purification using affinity columns have the following problems:
(1) The desired target substance is not selectively separated. That is, in addition to the target substance captured by the ligand, unwanted substances are also adsorbed onto the column.
(2) The capture efficiency is low, which means a large quantity of the liquid sample is required.

The affinity separation method in which affinity particles are dispersed in a liquid sample for separation uses agarose and such (Non-patent Document 1), but this method has the following problems:
(1) The desired target substance is not selectively separated. That is, in addition to the target substance captured by the ligand, unwanted target substances are also adsorbed onto the affinity particles.
(2) The specific gravity is small, which makes the separation of the affinity particles difficult.
(3) The carrier is easily disintegrated, which leads to poor durability.

On the other hand, inorganic particles adsorb more substances than organic particles do, therefore those skilled in the art didn't think of using inorganic particles for affinity particles.

Patent Document 1: Japanese Patent Publication H8-26076
Patent Document 2: Japanese Patent Laid-Open 2002-511141 bulletin Non-patent Document 1: Bioconjugate Chem.; 2002; 13(2); 163-166

DISCLOSURE OF INVENTION

Problem that the Present Invention Aims to Solve

The object of the present invention is to provide a groundbreaking affinity separation method that uses affinity particles utilizing inexpensive inorganic particles and is capable of separating the target substance easily and with high accuracy. The present invention is very useful in various separation, purification, and testing methods including latex agglutination methods and immunoprecipitation methods that allow easy and highly sensitive detection of the target substance.

Means to Solve the Problem

That is, the present invention provides affinity particles that are characterized by having phosphorylcholine groups represented by the following formula (1) covalently bonded onto the surface of inorganic particles.

[Chemical formula 4]

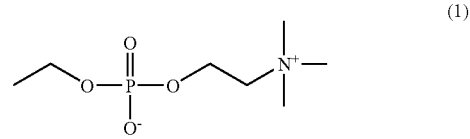

Also, the present invention provides affinity particles that are characterized by having phosphorylcholine groups represented by the following formula (1) covalently bonded onto the surface of inorganic particles and also by having reactive groups or adsorptive groups, which are capable of bonding with ligands having specific affinity with a certain target substance, covalently bonded or adsorbed onto the surface of inorganic particles.

[Chemical formula 5]

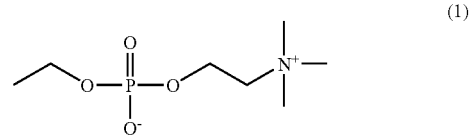

Furthermore, the present invention provides affinity particles that are characterized by having phosphorylcholine groups represented by the following formula (1) covalently bonded onto the surface of inorganic particles and also by having ligands having specific affinity with a certain target substance covalently bonded or adsorbed onto the surface of inorganic particles.

[Chemical formula 6]

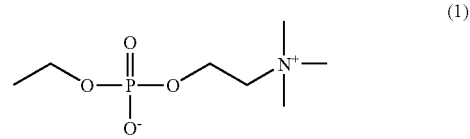

Also, the present invention provides the aforementioned affinity particles wherein said inorganic particles are selected from a group consisting of silica, titanium oxide, zinc flower, alumina, iron oxide, talc, mica, sericite, and gold colloid, and having an average particle size of 20 nm to 500 μm and a specific gravity of 1.0 g/cm$^3$ or higher.

Furthermore, the present invention provides the aforementioned affinity particles wherein said ligands are one, two, or more types of ligands chosen from a group consisting of various antibodies, antigens, enzymes, substrates, lectin, receptors, peptides, DNA, RNA, aptamers, protein A, protein G, avidin, biotin, chelating compounds, and various metal ions.

Also, the present invention provides a method of affinity separation of a target substance by using inorganic particles that includes (1) a first process whereby arbitrary ligands are bonded to the affinity particles of claim 1 or 2, (2) a second process whereby the affinity particles prepared in the first process are dispersed in a liquid sample containing a target substance selectively captured by the arbitrary ligands, and (3) a third process whereby the target substance captured is recovered from the affinity particles.

Furthermore, the present invention provides a method of affinity separation of a target substance by using inorganic particles that includes (1) a first process whereby the affinity particles of claim 3 are dispersed in a liquid sample containing a target substance selectively captured by the arbitrary ligands, and (2) a second process whereby the target substance captured is recovered from the affinity particles. When the affinity particles of the present invention are used for detection of antibodies and protein, such as in the immuno-precipitation method and the latex agglutination method, the recovery process (2) is not required; detection can be done easily by visually observing changes in the dispersion state.

EFFECTS OF THE INVENTION

The affinity particles of the present invention use ligands to capture only a certain target substance (the substance desired to be separated) and suppresses adsorption of other substances onto the particles, resulting in a very high separation selectivity. They also exhibit superior dispersion properties and make separation from liquid samples very easy, which makes it possible to separate the target substance easily and with high accuracy by using inexpensive inorganic powder particles for affinity particles.

That is, the target substance separation method of the present invention can effectively and easily separate the target substance to be separated in a short amount of time. Since substances have a tendency to adsorb onto foreign substances, conventional affinity particles have difficulties efficiently isolating only the target substance; however, it is possible to very efficiently prevent non-specific adsorption of other substances to the affinity particles and thus increase the purification yield by modifying the particle surface with phosphorylcholine groups.

Also, phosphorylcholine groups are extremely hydrophilic and they also improve the dispersion properties of the affinity particles in a liquid sample containing water.

Furthermore, conventional particles tend to aggregate in the presence of salts and therefore the purification efficiency decreases when the target substance is to be isolated from serum because of aggregation due to various salts in serum; however, the affinity particles of the present invention don't aggregate significantly even under the presence of salts, which makes it possible to recover the target substance efficiently.

The affinity particles used in the present invention are composed of inorganic particles and therefore their specific gravity is high, which makes it easy to recover them by leaving the mixture at rest or by light centrifugation. These particles can be filled in a column as carriers and such a column can be used as an affinity column to recover a target substance.

BEST MODE FOR CARRYING OUT THE INVENTION

Figure 1:
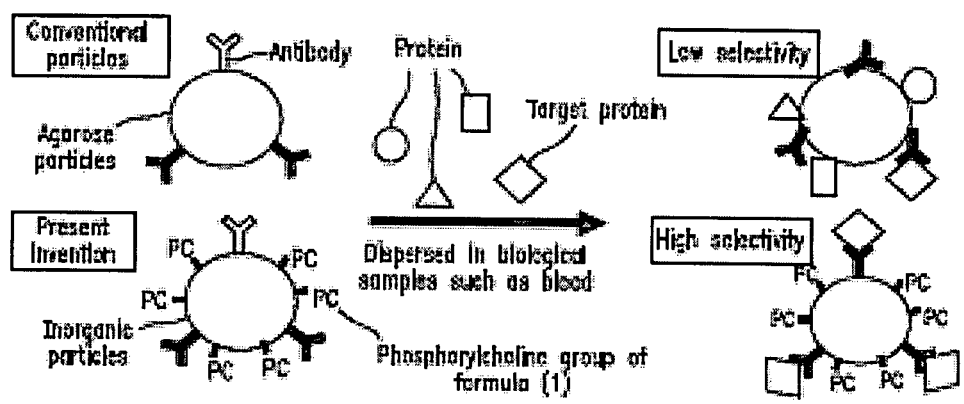
FIG. 1 is a schematic showing the difference between the protein capture selectivity of the affinity particles of the present invention and conventional affinity particles.

The present invention is described in detail below.
"Inorganic Particles"

The selection of the inorganic particles that constitute the affinity particles is not limited in particular in the present invention. "An inorganic particle" generally means any inorganic object having an average particle size of about 20 nm to 500 μm. for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, myristic acid zinc, calcium palmitate, and aluminum stearate), boron nitride, cerium oxide, and gold colloid.

Particularly preferable particles include silica, titanium oxide, zinc flower, alumina, iron oxide, talc, mica, sericite, and gold colloid. Nonporous inorganic particles are more preferable than porous inorganic particles.

Since the phosphorylcholine group represented by the aforementioned formula (1) and reactive groups or adsorptive groups that are capable of bonding with ligands are to be introduced onto the particle surface by means of covalent bonding, the surface should preferably have reactive groups such as amino groups.

Preferable affinity particles are those whose inorganic particles have an average particle size of 20 nm to 500 µm and a specific gravity of 1.0 g/cm$^3$ or higher.

Examples include silica, titanium oxide, zinc flower, alumina, iron oxide, talc, mica, sericite, and gold colloid.

"Reactive Groups or Adsorptive Groups to which the Ligand can Bind"

The selection is not limited as long as bonding with the ligand is possible. Preferable examples of the covalent bond form include an amide, ester, urethane, ether, secondary amine, urea bond, and disulfide bond. Therefore, reactive groups for which ligands can take the corresponding covalent bond forms are preferable; examples include amino groups, hydroxyl groups, carboxyl groups, thiol groups, and aldehyde groups. Also, for the adsorption form, preferable are an avidin-biotin, metal-chelating compound, etc. Therefore, adsorptive groups for which ligands can take the corresponding adsorptive forms are preferable; examples include avidin, biotin, and chelating compounds.

"Ligands"

In the present invention, a "ligand" means a substance that binds specifically to a certain target substance; examples include various antibodies, antigens, enzymes, substrates, receptors, peptides, DNA, RNA, aptamers, protein A, protein G, avidin, biotin, chelating compounds, and various metal ions. Examples of the various antibodies include IgG, IgM, IgA, IgD, IgE, and IgY, examples of antigens include protein and polysaccharides, examples of enzymes include glutathione-S-transferase, examples of substrates include glutathione, examples of receptors include hormone receptors and cytokine receptors, examples of chelating compounds include nitrile triacetate, and examples of various metal ions include $Ni^{2+}$, $Co^{2+}$, $Cu^{2+}$, $Zn^{2+}$, and $Fe^{3+}$.

"A Method of Preparing the Affinity Particles of the Present Invention"

Since the essence of the present invention is to have the phosphorylcholine group represented by formula (1) covalently bonded onto the surface of inorganic particles and also for the inorganic particles to have reactive groups or adsorptive groups capable of bonding to ligands having specific affinity to a certain target substance that are directly present on their surface by means of covalent bonding or adsorption, there is no limitation on the selection of the preparation method; bonding can be done by any means.

However, as mentioned earlier, this does not include methods in which a polymer already having the phosphorylcholine group and reactive groups or adsorptive groups capable of bonding to ligands is used to simply coat the particle surface without chemical bonding. This is because the coating polymer can peel off and/or there may be an influence from the coating polymer.

The affinity particles of the present invention can be prepared with the following method, for example.

Step 1: The phosphorylcholine group represented by the following formula (1) and reactive groups or adsorptive groups capable of bonding to ligands are introduced onto the particles. The selection of the reactive group or adsorptive group is not limited; examples include an amino group, hydroxyl group, carboxyl group, and aldehyde group.

Step 2: The phosphorylcholine group represented by formula (1) and the ligand are bonded to the reactive group or adsorptive group introduced onto the particles. Any chemical structure (spacer) can exist between the phosphorylcholine group or ligand and the reactive group or adsorptive group. Examples of such arbitrary spacers include a methylene chain, oxyethylene chain, as well as an alkylene chain containing one or a plurality of amino groups.

"When the Reactive Group or Adsorptive Group on the Particle Surface is an Amino Group"

Step 1: Amino groups are introduced to any particle by using a prior art method or a method that will be developed in the future. Amino groups are directly introduced onto the particle surface. The amino group can be a primary amine or a secondary amine.

Step 2: An aldehyde derivative or hydrate derivative obtained by the oxidative cleavage reaction of glycerophosphorylcholine is used in a reductive amination reaction to directly add phosphorylcholine groups to the surface of the particle having amino groups.

Not all the amino groups are bonded with the phosphorylcholine group (the reaction level is controlled) so that the remaining amino groups are available as substituents for the ligand to bind to.

Or, a carboxyl derivative obtained by the oxidative cleavage reaction of glycerophosphorylcholine is used in an amidation reaction to directly add phosphorylcholine groups to the surface of the particles having amino groups.

Not all the amino groups are bonded with the phosphorylcholine group (the reaction level is controlled) so that the remaining amino groups are available as substituents for the ligand to bind to.

"A Method of Introducing Amino Groups onto the Particle Surface"

Examples of a prior art method for introducing amino groups to the particles (step 1) follow:

1. Introduction of Amino Groups by Means of a Surface Reaction Via a Plasma Treatment Amino groups are introduced to the particle surface by means of a low temperature plasma in a nitrogen gas atmosphere. Specifically, the particles are put into a plasma reactor vessel and, after a vacuum pump is used to form a vacuum in the reactor vessel, nitrogen gas is introduced. Amino groups can be then introduced onto the particle surface by means of glow discharge. It is also possible to mechanically turn the plasma-treated inorganic material into particles. References related to the plasma treatment are shown below:

1. M. Muller, C. oehr
   Plasma aminofunctionalisation of PVDF microfiltration membranes: comparison of the in plasma modifications with a grafting method using ESCA and an amino-selective fluorescent probe Surface and Coatings Technology 116-119 (1999) 802-807
2. Lidija Tusek, Mirko Nitschke, Carsten Werner, Karin Stana-Kleinschek, Volker Ribitsch Surface characterization of NH3 plasma treated polyamide 6 foils
   Colloids and Surfaces A: Physicochem. Eng. Aspects 195 (2001) 81-95
3. Fabienne Poncin-Epaillard, Jean-Claude Brosse, Thierry Falher Reactivity of surface groups formed onto a plasma treated poly (propylene) film
Macromol. Chem. Phys. 200. 989-996 (1999)

2. Introduction of Amino Groups by Means of a Surface Modifier

The surface of the inorganic particles such as silanol-containing particles is treated with a surface modifier having amino groups, such as alkoxysilane, chlorosilane, and silazane.

For example, silica particles are treated with 3-aminopropyltrimethoxysilane, which has a primary amino group, to introduce amino groups. Specifically, silica is soaked in a mixed solution of water and 2-propanol, and, after adding 3-aminopropyltrimethoxysilane, the temperature is raised to 100° C. and the reaction is carried out for six hours. After cooling down to room temperature, the silica is rinsed with methanol and dried to obtain particles that have amino groups directly introduced onto the silica surface. In addition to silica, examples of the particles preferably treated with this method include particles composed of glass, alumina, talc, clay, aluminum, iron, mica, asbestos, titanium oxide, zinc flower, and iron oxide.

3. Introduction of Amino Groups by Means of the Silicone Vapor Phase Treatment (Refer to Japanese Patent Publication No. H1-54379, Japanese Patent Publication No. H1-54380 bulletin, and Japanese Patent Publication No. H1-54381 Bulletin.)

The particle surface is treated with 1.3.5.7-tetramethylcyclotetrasiloxane and then Si—H groups introduced onto the surface are reacted with monomers having an amino group to obtain an aminated surface. For example, mica and 1.3.5.7-tetramethylcyclotetrasiloxane are put into a desiccator and an aspirator is used to deaerate it. The reaction is carried out for 16 hours at 80° C., and the mica is taken out and dried at 120° C. The obtained mica is dispersed in ethanol, to which allylamine is added, and an ethanol solution of chloroplatinic acid is added, followed by two hours of stirring at 60° C. After the reaction is completed, filtration, ethanol rinsing, and reduced-pressure drying is carried out to obtain aminated mica. Various inorganic particles (mica, talc, kaolin, alumina, titanium oxide, zinc oxide, iron oxide, various inorganic pigments, etc.) are preferably treated.

For the monomer to be used in this method, an amine-type monomer can be used. The amine-type monomer is not limited to allylamine as long as it has a reactive site such as polymerizable vinyl and acrylate, and an amino group. The amino group can be protected by a butoxycarbonyl group, benzyloxycarbonyl group or the like.

In addition to an amine-type monomer, a monomer having a functional group such as an epoxy group, to which an amino group can be easily introduced by means of, for example, a reaction with diamine, can be used as well.

"A Method for Introducing Phosphorylcholine Groups Onto the Particles Having Amino Groups"

Next, a method for introducing phosphorylcholine groups onto the aminated particle surface (step 2) is described below.

The particles are soaked in methanol, to which phosphatidylglyceroaldehyde is added, and the mixture is left alone for six hours at room temperature. Sodium cyanoborate is then added at 0° C., followed by overnight heating and stirring, to add a phosphorylcholine group to an amino group. The particles are rinsed with methanol and dried to obtain particles that have phosphorylcholine groups directly on the surface. For the reaction solvent, protic solvents such as water, ethanol, and 2-propanol can be used in addition to methanol; the introduction rate tends to be higher when methanol is used.

Shown below is a scheme in which amino groups are introduced onto silica by using 3-aminopropyl trimethoxysilane as the surface modifier and then phosphorylcholine groups (abbreviated as PC) are introduced.

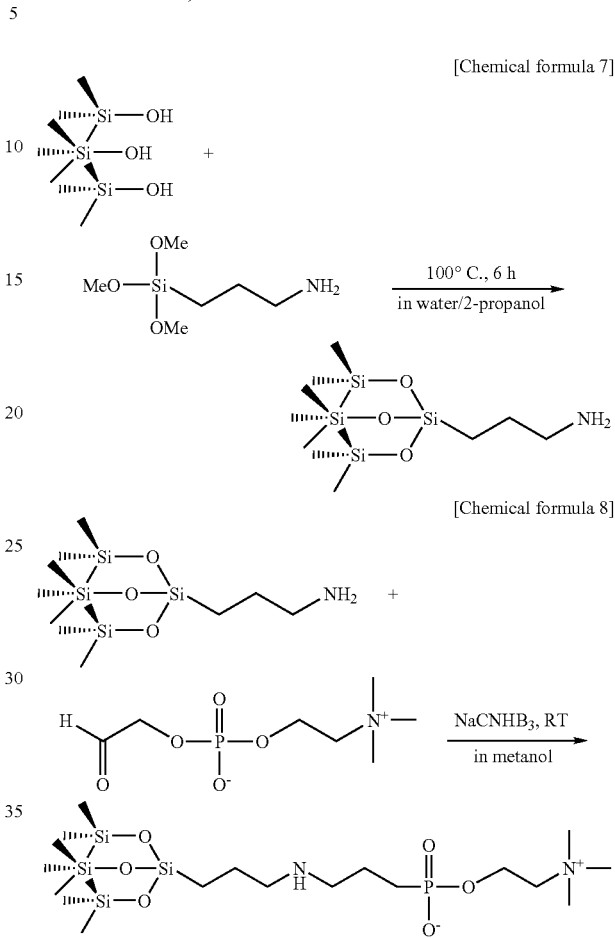

As described above, the particles directly having phosphorylcholine groups on the surface can be obtained by a method in which particles having amino groups are prepared and then a reductive amination reaction with a hydrate derivative or aldehyde derivative obtained by the oxidative cleavage reaction of glycerophosphorylcholine is used to directly add phosphorylcholine groups to the particle surface.

This method has the following great advantages: the introduction rate of the phosphorylcholine group is high, and the surface of various inorganic particles can be modified.

The aforementioned compound containing aldehyde is obtained by oxidative cleavage of the prior art glycerophosphorylcholine group by means of a prior art method, which is a very easy step. For example, 1,2-diol is oxidized with an oxidant such as periodic acid, periodate, or bismuth trioxide to cleave the bond and obtain an aldehyde derivative. The reaction is usually carried out in water or an organic solvent containing water at a reaction temperature between 0° C. and room temperature. The aldehyde derivative may go through an equilibrium reaction in water to become a hydrate, but this does not affect the subsequent reaction with the amine. An example of a scheme for preparing a monofunctional aldehyde derivative containing a phosphorylcholine group is described below.

[Chemical formula 9]

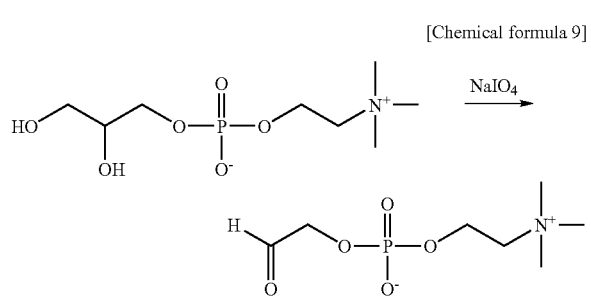

The reductive amination reaction for bonding the aldehyde derivative (or hydrate derivative) obtained by the oxidative cleavage reaction of glycerophosphorylcholine to the amino groups of the particles can be carried out easily by stirring both of them in a solvent. This reaction is carried out by dissolving or dispersing these two in water or alcohol (a third organic solvent ingredient can be mixed in, too) to form an imine and reducing it with a reducing agent to obtain a secondary amine. For the reducing agent, a mild reducing agent such as sodium cyanoboronate is preferable, but other reducing agents can be used as long as the phosphorylcholine is stable. The reaction is usually carried out at 0° C. to room temperature, but heating may be done depending on the situation.

It is also possible to react any amount of the compound represented by formula (2) to the aforementioned amino groups and leave the remaining amino groups as reactive groups or adsorptive groups to which ligands can bind.

[Chemical formula 10]

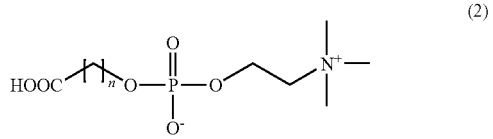

(2)

n denotes an integer 1-12.

Examples of the specific methods include a method in which the compound of formula (2) is reacted with thionyl chloride in N,N'-dimethylformamide to obtain an acid chloride, which is then reacted with particles having amino groups in N,N'-dimethylformamide to introduce the phosphorylcholine group represented by formula (1) by means of amide bonding.

The compound of formula (2) can be synthesized by using the following scheme.

"Reactive Groups or Adsorptive Groups to which Ligands can Bind"

Not all the amino groups are bonded with the phosphorylcholine group (the reaction level is controlled) so that the remaining amino groups are available as reactive groups or adsorptive groups for the ligand to bind to. These particles are the affinity particles described in claim 2, i.e. the particles that are inorganic particles directly having on their surface the phosphorylcholine groups represented by formula (1) and reactive groups or adsorptive groups to which the ligand can bond. When the ligand is bonded to these remaining amino groups, the affinity particles described in claim 3, i.e. the inorganic particles directly having the phosphorylcholine group represented by formula (1) and the ligand on their surface, are obtained.

The product form of the affinity particles described in claim 2 is such that the user can bond any ligand to them depending on the substance to be captured (target substance). The product form of the affinity particles described in claim 3 is such that the ligand is already bonded. The affinity particles described in claim 1 are affinity particles having at least the phosphorylcholine group of formula (1) on the particle surface and their product form is such that the user can bind any ligand to them depending on the substance to be captured (target substance), regardless of the presence or absence of the ligand or reactive group or adsorptive group that can bind to it. Affinity particles of any form are included as long as the phosphorylcholine group of formula (1) is present on the particle surface; for example, the forms described in claim 2 and claim 3 are included as well.

In the aforementioned reaction, leaving some amino groups as reactive groups or adsorptive groups to which the ligand can bind can be made possible, for example, by adjusting the reaction quantity or by a competitive reaction of 3-aminopropyl trimethoxysilane and 3-aminopropyl trimethoxysilane to which the phosphorylcholine group is introduced.

It is also possible to react this amino group with a compound having any functional group and use this functional group as the reactive group or adsorptive group to which the ligand can bind. Examples include glutaraldehyde, alkyl diimidate, acyl azides, and isocyanates.

In a scheme in which 3-aminopropyl trimethoxysilane is used for the aforementioned surface modifier, it is also possible to adjust the reaction quantity of the surface modifier to leave some hydroxyl groups (OH) on the particle surface and use these remaining OH groups as reactive groups or adsorptive groups to which the ligand can bind.

"A Method of Binding the Ligand to the Particles having Amino Groups"

When the ligand is a protein, one aldehyde group of glutaraldehyde is reacted with an amino group on the inorganic particle and the other aldehyde group is reacted with an amino group in the protein, thus binding the protein.

"When the Reactive Group or Adsorptive Group on the Particle Surface is a Hydroxyl Group"

Since most inorganic particles have hydroxyl groups on their surface, no reactive group or adsorptive group to which the ligand can bind, such as amino groups as mentioned above, needs to be introduced; the hydroxyl groups (OH) present on the particle surface are used as they are to introduce the phosphorylcholine group and the ligand or reactive groups or adsorptive groups to which the ligand can bind. The affinity particles of the present invention are preferably prepared with this method.

"A Method for Introducing Phosphorylcholine Groups onto the Particles Having Hydroxyl Groups"

A chemical bond is formed by dehydration of the hydroxyl group on the particle surface and Si—OMe of the compound of the following formula (3) or (4). This chemical reaction proceeds very easily and quantitatively in most organic solvents if heating and refluxing are provided. Chemically and physically very stable phosphorylcholine groups can be introduced by means of this dehydration reaction, which is preferable. The phosphorylcholine group-containing compound represented by the following formula (3) or (4) is a new compound.

[Chemical formula 11]

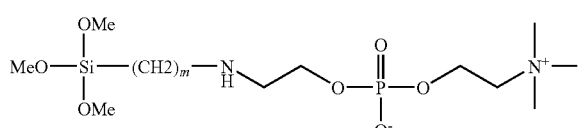
(3)

[Chemical formula 11]

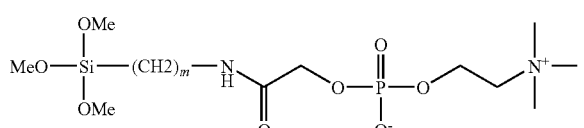
(4)

In this formula, m denotes 2-6 and n denotes 1-4. OMe can be replaced by OEt or Cl. Up to two of the OMe's, OEt's, or Cl's to be bonded to Si can be replaced by a methyl group, ethyl group, propyl group, isopropyl group, or isobutyl group.

"A Method of Preparing the Phosphorylcholine Group-Containing Chemical Compound of Formula (3)"

The phosphorylcholine derivative shown in the following formula (5) is dissolved in distilled water. The phosphorylcholine derivative of the following formula (5) is a prior art chemical compound and commercially available.

[Chemical formula 13]

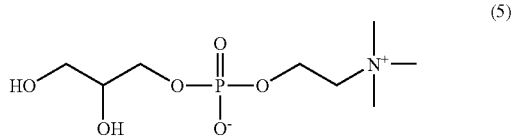
(5)

An aqueous solution of the chemical compound of formula (5) is cooled in an ice water bath; then sodium periodate is added, followed by five hours of stirring. The reaction fluid is concentrated under reduced pressure and dried under reduced pressure; methanol is used to extract a phosphorylcholine derivative having an aldehyde group shown in the following formula (6).

[Chemical formula 14]

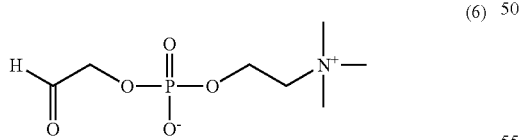
(6)

0.5 equivalents of 3-aminopropyltrimethoxysilane is added to the methanol solution of formula (6). This mixed solution is stirred for a prescribed amount of time at room temperature and cooled with ice; an appropriate amount of sodium cyanohydroborate is then added and the temperature is returned back to room temperature, followed by 16 hours of stirring. During this time dry nitrogen is continued to be fed through the reaction vessel. After filtering the precipitate, a methanol solution of formula (3) and/or (4) is obtained.

The procedure described above can be carried out in the exact same way even when m and n in the chemical compounds represented by formula (3) or (4) change. The procedure shown here is for m=3 and n=2. The reaction solvent is not limited in particular; in addition to methanol, which was mentioned above, water, alcohols such as ethanol, propanol, and butanol, and aprotic solvents such as DMF and DMSO can be used. Dehydrated solvents are preferable to prevent polymerization during the reaction; of these, dehydrated methanol is particularly preferable.

If a methoxy group (OMe) in formula (3) or (4) is replaced by an ethoxy group (OEt), then the reaction is carried out by using ethanol instead of methanol; if it is replaced by Cl, then dimethylformamide or dimethylsulfoxide is used instead.

Furthermore, even when one or two of the OMe groups, OEt, or Cl's to be bonded to Si are replaced by a methyl group, ethyl group, propyl group, butyl group, isopropyl group, or isobutyl group, the preparation can be carried out in exactly the same manner as described above.

"A Method of Preparing the Phosphorylcholine Group-Containing Chemical Compound of Formula (4)"

The phosphorylcholine derivative shown in the following formula (5) is dissolved in a mixture of distilled water and acetonitrile. The phosphorylcholine derivative of the following formula (5) is a prior art chemical compound and commercially available.

[Chemical formula 15]

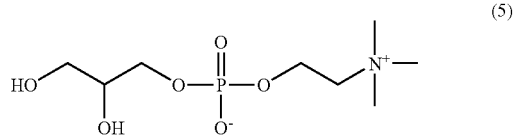
(5)

An aqueous solution of the chemical compound of formula (5) is cooled in an ice water bath; sodium periodate and ruthenium trichloride are added, followed by three hours of stirring. The reaction fluid is concentrated under reduced pressure and dried under reduced pressure; methanol is used to extract a phosphorylcholine derivative having an carboxyl group shown in the following formula (7).

[Chemical formula 16]

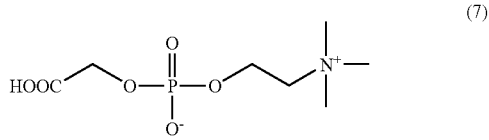
(7)

Thionyl chloride is then added to formula (7) in N,N'-dimethylformamide to turn it into an acid chloride, to which 0.5 equivalents of 3-aminopropyltrimethoxysilane and 2 equivalents of triethylamine are added. This mixed solution is stirred at room temperature for a prescribed amount of time to obtain an N,N'-dimethylformamide solution of formula (4).

The procedure described above can be carried out in the same way even when m and n in the chemical compounds represented by formula (4) change. The procedure shown here is for m=3 and n=2. The reaction solvent is not limited in particular; in addition to N,N'-dimethylformamide, which was mentioned above, aprotic solvents such as acetonitrile, tetrahydrofuran, and dimethylsulfoxide can be used. It is preferable to use a dehydrated solvent to prevent polymerization during the reaction.

Furthermore, even when one or two of the OMe groups, OEt, or Cl's to be bonded to Si are replaced by a methyl group, ethyl group, propyl group, isopropyl group, butyl group, or isobutyl group, the preparation can be carried out in exactly the same manner as described above.

"Reactive Groups or Adsorptive Groups to which Ligands can Bind"

Not all the hydroxyl groups are bonded with the phosphorylcholine group (the reaction level is controlled) so that the remaining hydroxyl groups are available as reactive groups or adsorptive groups for the ligand to bind to. These particles are the affinity particles described in claim 2, i.e. the particles that are inorganic particles directly having on their surface the phosphorylcholine groups represented by formula (1) and reactive groups or adsorptive groups to which the ligand can bond. When the ligand is bonded to these remaining hydroxyl groups, the affinity particles described in claim 3, i.e. the inorganic particles directly having the phosphorylcholine group represented by formula (1) and the ligand on their surface, are obtained.

The product form of the affinity particles described in claim 2 is such that the user can bond any ligand to them depending on the substance to be captured (target substance). The product form of the affinity particles described in claim 3 is such that the ligand is already bonded. The affinity particles described in claim 1 are affinity particles having at least the phosphorylcholine group of formula (1) on the particle surface and their product form is such that the user can bind any ligand to them depending on the protein to be captured (target substance), regardless of the presence or absence of the ligand or reactive group or adsorptive group that can bind to the ligand. Affinity particles of any form are included as long as the phosphorylcholine group of formula (1) is present on the particle surface; for example, the forms described in claim 2 and claim 3 are included as well.

"A Method of Binding the Ligand to the Particles having Hydroxyl Groups"

When the ligand is a protein, hydroxyl groups on the particles are activated by using cyanogen bromide. Amino groups in the protein are reacted with these to bind the protein.

It is also possible to react this hydroxyl group with a compound having any functional group and use this functional group as the reactive group or adsorptive group to which the ligand can bind.

"When the Reactive Group or Adsorptive Group on the Particle Surface is a Carboxyl Group"

Step 1: Carboxyl groups are introduced to any particle by using a prior art method or a method that will be developed in the future. Carboxyl groups are directly introduced onto the particle surface.

Step 2: It is also possible to react the phosphorylcholine-containing compound represented by formula (2) with the particles having carboxyl groups so as to form an acid amide bonding with the phosphorylcholine group and use the remaining carboxyl groups as reactive groups or adsorptive groups to which ligands can bind.

Not all the carboxyl groups are bonded with the phosphorylcholine group (the reaction level is controlled) so that the remaining carboxyl groups are available as reactive groups or adsorptive groups for the ligand to bind to.

[Chemical formula 17]

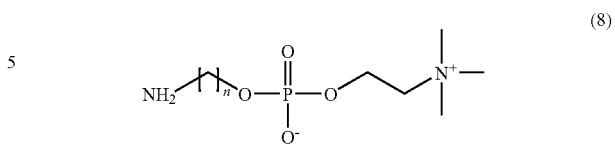

(8)

"A Method of Introducing Carboxyl Groups onto the Particle Surface"

Examples of a prior art method for introducing carboxyl groups to the particles (step 1) follow:

1. Introduction of Carboxyl Groups by Means of a Surface Modifier

The surface of the inorganic particles such as silanol-containing particles is treated with a surface modifier having carboxyl groups, such as alkoxysilane, chlorosilane, and silazane.

For example, silica particles are treated with triethoxysilylpropyl succinate anhydride to introduce carboxyl groups. Specifically, triethoxysilylpropyl succinate anhydride is dissolved in N,N-dimethylformamide, to which distilled water and 4-dimethylaminopyridine is added, followed by stirring at room temperature for 16 hours to obtain a silane coupling agent having carboxylic acid represented in the following formula (3). This reaction is a hydrolysis reaction of succinic acid anhydrate using 4-dimethylaminopyridine.

Silica particles are treated with the silane coupling agent having carboxyl groups to introduce carboxyl groups. Specifically, silica is soaked in a mixed solution of water and 2-propanol, and, after adding the silane coupling agent having carboxyl groups, the temperature is raised to 100° C. and the reaction is carried out for six hours. After cooling down to room temperature, the silica is rinsed with methanol and dried to obtain particles that have carboxyl groups directly introduced onto the silica surface. In addition to silica, examples of the particles preferably treated with this method include particles composed of glass, alumina, talc, clay, aluminum, iron, mica, asbestos, titanium oxide, zinc flower, and iron oxide.

2. Introduction of Carboxyl Groups by Means of the Silicone Vapor Phase Treatment (Refer to Japanese Patent Publication No. H1-54379, Japanese Patent Publication No. H1-54380 bulletin, and Japanese Patent Publication No. H1-54381 Bulletin.)

The particle surface is treated with 1.3.5.7-tetramethylcyclotetrasiloxane and then Si—H groups introduced onto the surface are reacted with monomers having a carboxyl group to obtain a carboxylated surface. Various inorganic particles (mica, talc, kaolin, alumina, titanium oxide, zinc oxide, iron oxide, various inorganic pigments, etc.) are preferably treated.

For the monomer to be used in this method, a carboxyl-type monomer can be used. The selection of the carboxyl-type monomer is not limited as long as it has a reactive site such as a carboxyl group, polymerizable vinyl and acryl.

"A Method for Introducing Phosphorylcholine Groups onto the Particles having Carboxyl Groups"

Next, a method for introducing phosphorylcholine groups onto the carboxylated particle surface (step 2) is described below.

When particles having carboxyl groups on the surface are soaked in a solution of N-hydroxysuccinimide and 1-ethyl-3-(3-dimethylaminopropyl)-carbodiimide, the particle surface is coated with active ester groups. A solution of the phosphorylcholine derivative having an amino group represented by formula (7) is added to this to introduce phosphorylcholine groups.

"Reactive Groups or Adsorptive Groups to which Ligands can Bind"

Not all the carboxyl groups are bonded with the phosphorylcholine group (the reaction level is controlled) so that the remaining carboxyl groups are available as reactive groups or adsorptive groups for the ligand to bind to. These particles are the affinity particles described in claim 2, i.e. the particles that are inorganic particles directly having on their surface the phosphorylcholine groups represented by formula (1) and reactive groups or adsorptive groups to which the ligand can bond. When the ligand is bonded to these reactive or adsorptive groups to which the ligand can bind, the affinity particles described in claim 3, i.e. the inorganic particles directly having the phosphorylcholine group represented by formula (1) and the ligand on their surface, are obtained.

The product form of the affinity particles described in claim 2 is such that the user can bond any ligand to them depending on the substance to be captured (target substance). The product form of the affinity particles described in claim 3 is such that the ligand is already bonded. The affinity particles described in claim 1 are affinity particles having at least the phosphorylcholine group of formula (1) on the particle surface and their product form is such that the user can bind any ligand to them depending on the substance to be captured (target substance), regardless of the presence or absence of the ligand or reactive group or adsorptive group that can bind to the ligand. Affinity particles of any form are included as long as the phosphorylcholine group of formula (1) is present on the particle surface; for example, the forms described in claim 2 and claim 3 are included as well.

In the aforementioned reaction, leaving some carboxyl groups as reactive groups or adsorptive groups to which the ligand can bind can be made possible, for example, by adjusting the reaction quantity of the silane coupling agent having a carboxylic acid to which the phosphorylcholine group is introduced.

It is also possible to react this carboxyl group with a compound having any functional group and use this functional group as the reactive group or adsorptive group to which the ligand can bind.

"A Method of Binding the Ligand to the Particles having Carboxyl Groups"

When the ligand is a protein, inorganic particles having carboxyl groups on the surface are soaked in a solution of N-hydroxysuccinimide and 1-ethyl-3-(3-dimethylaminopropyl)-carbodiimide to esterify the particle surface. Amino groups in the protein are reacted with these to bind the protein. It is also possible to react this hydroxyl group with a compound having any functional group and use this functional group as the reactive group or adsorptive group to which the ligand can bind.

"A Method of Affinity Separation of a Target Substance"

Using the affinity particles of the present invention obtained as described above, the affinity separation of a target substance of the present invention is carried out.

The method of the present invention is a groundbreaking separation/purification method for a target substance in that high precision separation can be easily done by using inorganic particles.

The method of the present invention contains the following 3 processes. The first process is omitted for the affinity particles to which the ligand is already bonded (claim 2) since this process has already been done for such particles.

1. The first process in which any ligand is chemically bonded to affinity particles that are characterized by having phosphorylcholine groups represented by the following formula (1) covalently bonded onto the surface of inorganic particles or affinity particles that are characterized by having phosphorylcholine groups represented by the following formula (1) covalently bonded onto the surface of inorganic particles and also by having reactive groups or adsorptive groups, that are capable of bonding with ligands having specific affinity with a certain target substance, covalently bonded or adsorbed onto the surface of inorganic particles.

For example, 1 ml of a PBS solution of any ligand and affinity particles that are inorganic particles having the phosphorylcholine group represented by formula (1) covalently bonded onto their surface and reactive groups or adsorptive groups to which the ligand can bind covalently bonded or adsorbed on their surface are put into a 2 ml eppen tube, followed by gentle shaking at 4° C. for 30 minutes. This is centrifuged for 5 minutes at 5000 rpm and the supernatant is discarded. The sample is cleaned by adding 1 ml of a PBS solution to it, gently shaking it, centrifuging it for 5 minutes at 5000 rpm, and discarding the supernatant. This cleaning operation is repeated 3 times.

2. The second process in which the affinity particles prepared in the first process are dispersed in a liquid sample containing the target substance that is selectively captured by any ligand.

For example, the affinity particles prepared in the first process are dispersed in a liquid sample containing the target substance that is selectively captured by any ligand, followed by gentle shaking for 30 minutes at 4° C. This is centrifuged for 5 minutes at 5000 rpm and the supernatant is discarded. The sample is cleaned by adding 1 ml of a PBS solution to it, gently shaking it, centrifuging it for 5 minutes at 5000 rpm, and discarding the supernatant. This cleaning operation is repeated 3 times.

3. The third process in which the captured target substance is recovered from the separated affinity particles.

For example, for the purpose of recovering the captured target substance from the affinity particles, 1 ml of an elution buffer is added, followed by gentle shaking for 30 minutes at 4° C. to elute the target substance from the particles, and the supernatant is recovered. 1 ml of a PBS solution is added to it, followed by gentle shaking and centrifugation for 5 minutes at 5000 rpm, and the supernatant is recovered. This operation is repeated twice.

FIG. 1 is a schematic showing the differences between the target substance capture selectivity of the affinity particles of the present invention and conventional affinity particles.

EXAMPLES

Next, the present invention is described in detail by referring to Examples. The present invention is not limited to these Examples. The phosphorylcholine groups introduced onto the particle surface can be verified and quantified by the FT-IR and element analysis.

Synthesis Example 1

"An Aldehyde Chemical Compound Containing Phosphorylcholine Groups"

1-alpha-glycerophosphorylcholine (6.29 g) was dissolved in 210 ml of distilled water and cooled in an ice water bath. Sodium periodate (10.23 g) was added, followed by five hours of stirring. The reaction fluid was concentrated under reduced pressure and dried under reduced pressure; methanol was then used to extract the target substance. The structure is shown in the following chemical formula (6).

Figure 2:
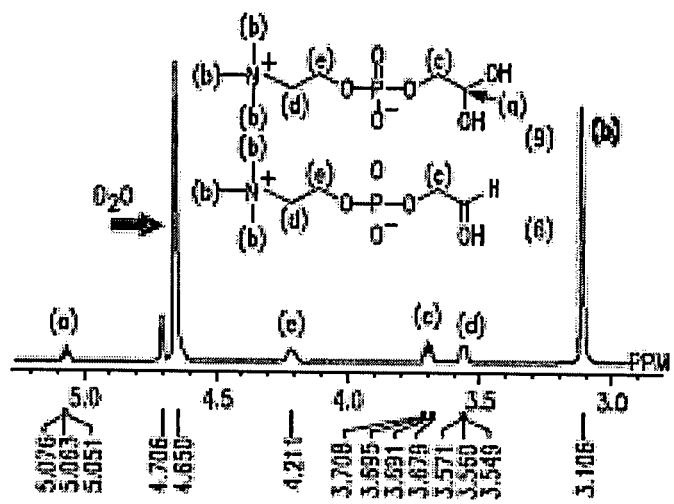
FIG. 2 shows a chemical structure formula and an NMR spectrum of the chemical compound prepared in Synthesis example 1.

A $^1$H NMR spectrum of the compound of formula (6) is shown in FIG. 2. Since the compound of formula (6) is in equilibrium with formula (9) in water, the actual spectrum reflects both formula (6) and formula (9).

[Chemical formula 18]

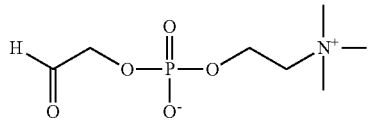

(6)

[Chemical formula 19]

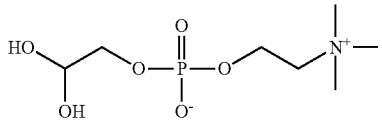

(9)

Synthesis Example 2

"A Carboxylic Acid Chemical Compound Containing Phosphorylcholine Groups"

5 g of glycerophosphorylcholine, 17 g of sodium periodate, 81 mg of ruthenium trichloride n-hydrate, 70 g of ion-exchanged water and 30 g of acetonitrile were put into a 200 ml flask. After stirring for two hours at room temperature, filtering was carried out and the solvent was removed from the filtrate. Methanol was used to extract the target compound from the obtained solid product; methanol was then removed to obtain the target compound (7).

Figure 3:
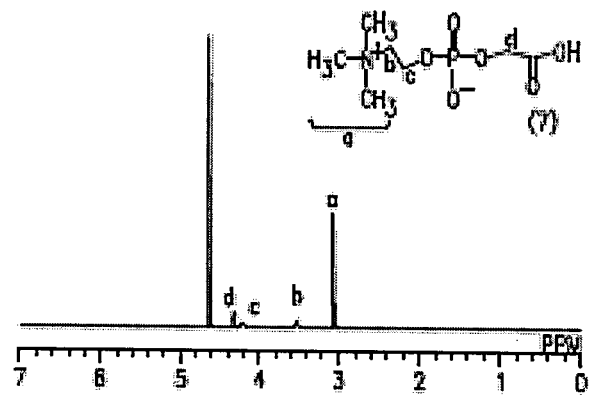
FIG. 3 shows a chemical structure formula and an NMR spectrum of the chemical compound prepared in Synthesis example 2.

A $^1$H NMR spectrum of the compound of formula (7) is shown in FIG. 3.

[Chemical formula 20]

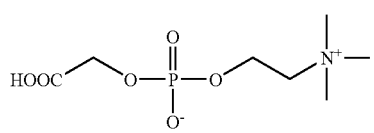

(7)

Synthesis Example 3

"Compound of Formula (10)"

9.0 g of the compound of Synthesis example 1 was dissolved in 55 mL of dehydrated methanol, and the air inside the vessel was replaced by dry nitrogen. Next, 2.84 g of 3-aminopropyltrimethoxysilane was added to the methanol solution of chemical compound 1. This mixed solution was stirred overnight at room temperature and cooled with ice; 1.39 g of sodium cyanohydroborate was then added and the temperature was returned back to room temperature, followed by 5 hours of stirring. During this time dry nitrogen was continued to be fed through the reaction vessel. After filtering the precipitation, a methanol solution of the target substance, i.e. the compound of the following formula (10), was obtained.

[Chemical formula 21]

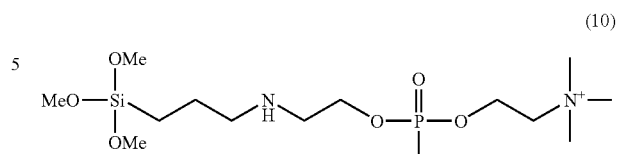

(10)

Synthesis Example 4

"Compound of Formula (11)"

5.0 g of the compound of Synthesis example 4 was dissolved in 300 mL of N,N'-dimethylformamide, and the air inside the vessel was replaced by dry nitrogen. 4.5 g of thionyl chloride was then added, followed by 15 minutes of stirring, after which 2.84 g of 3-aminopropyltrimethoxysilane and 9.5 g of triethylamine were added. This mixed solution was stirred at room temperature overnight and the precipitate was filtered to obtain an N,N'-dimethylformamide solution containing the target substance, i.e. the compound of the following formula (11).

[Chemical formula 22]

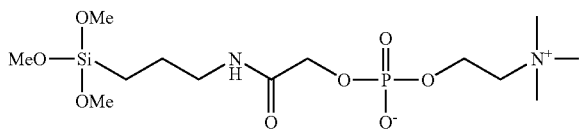

(11)

Reference Example 1

"Phosphorylcholine Particles (PC Particles (A)) that are Inorganic Particles having Phosphorylcholine Groups Covalently Bonded onto their Surface"

Figure 4:
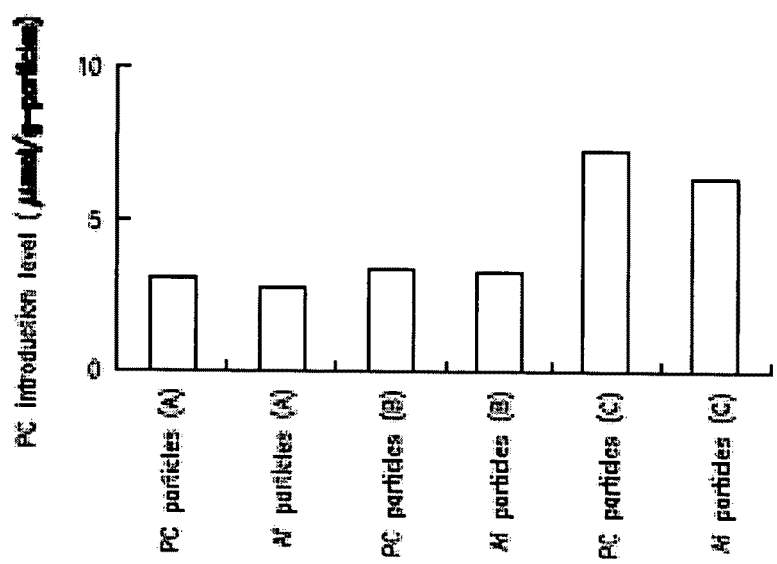
FIG. 4 shows the result of the P quantification using the PC particles (A), (B), and (C) prepared in Synthetic example 5 and the Af particles (A), (B), and (C) prepared in Synthetic example 6.

97.7 g μl of a methanol solution containing 50 μmol of the compound of formula (10) prepared in Synthesis example 3 was sampled, to which 47.5 ml of methanol and 2.5 ml of distilled water were added, and then 5 g of silica gel having an average particle size of 1.5 μm and a specific surface area of 6 m$^2$/g was added. This particle dispersion was refluxed at 80° C. overnight for coupling. After the refluxing, the particles were cleaned by means of centrifugation using methanol to obtain the PC particles of claim 1 (hereafter "PC particles (A)"). FIG. 4 shows the P quantification measurements of the PC-treated particles (A) prepared in the aforementioned procedure using the surface modifier of Synthetic example 3. The PC introduction level thus determined was 3.1 μmol/g-particles, which confirmed the introduction of PC groups onto the particle surface.

Reference Example 2

"Phosphorylcholine Particles (PC Particles (B)) that are Inorganic Particles having Phosphorylcholine Groups Covalently Bonded onto their Surface"

278 μl of a dimethylformamide solution containing 50 μmol of the compound of formula (11) prepared in Synthesis example 4 was sampled, to which 50 ml of dimethylformamide was added, and then 5 g of silica gel having an average particle size of 1.5 μm and a specific surface area of 6 m$^2$/g was added. This particle dispersion was refluxed at 160° C.

overnight for coupling. After the refluxing, the particles were cleaned by means of centrifugation using methanol to obtain the PC particles of claim 1 (hereafter "PC particles (B)"). FIG. 4 shows the P quantification measurements of the PC-treated particles (B) prepared in the aforementioned procedure using the surface modifier of Synthetic example 4. The PC introduction level thus determined was 3.4 µmol/g-particles, which confirmed the introduction of PC groups onto the particle surface.

Reference Example 3

"Phosphorylcholine Particles (PC Particles (C)) that are Inorganic Particles having Phosphorylcholine Groups Covalently Bonded onto their Surface"

278 µl of a dimethylformamide solution containing 50 µmol of the compound of formula (11) prepared in Synthesis example 4 was sampled, to which 47.5 ml of dimethylformamide and 2.5 ml of distilled water were added, and then 5 g of silica gel having an average particle size of 1.5 µm and a specific surface area of 6 m$^2$/g was added. This particle dispersion was refluxed at 160° C. overnight for coupling. After the refluxing, the particles were cleaned by means of centrifugation using methanol to obtain the PC particles of claim 1 (hereafter "PC particles (C)"). FIG. 4 shows the P quantification measurements of the PC-treated particles (C) prepared in the aforementioned procedure using the surface modifier of Synthetic example 4. The PC introduction level thus determined was 7.3 g mol/g-particles, which confirmed the introduction of PC groups onto the particle surface.

Figure 5:
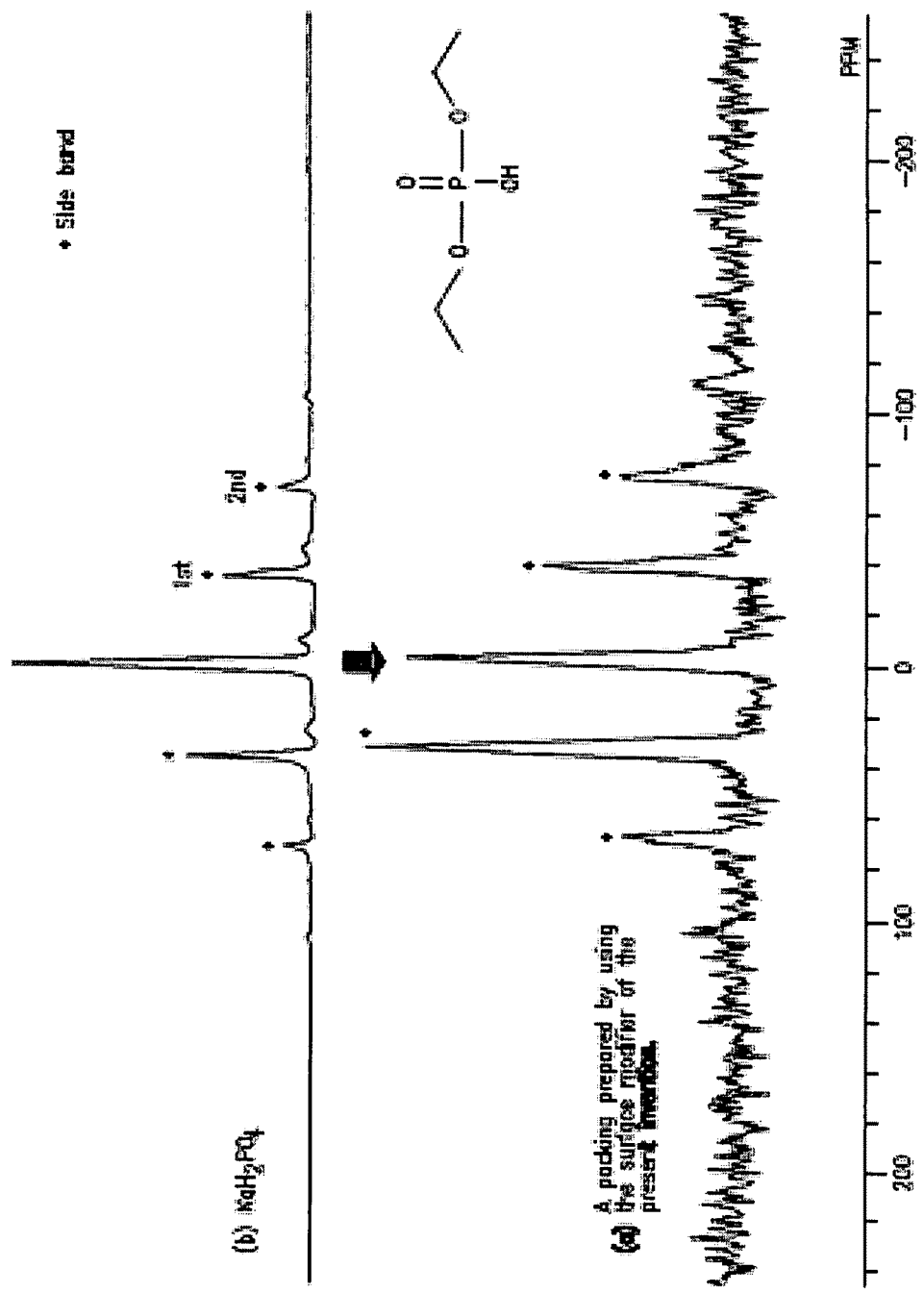
FIG. 5 is a 31P-CPMAS spectrum of the PC particles (A) prepared in Reference example 1.

A 13C-CPMAS spectrum and a 13C-PSTMAS spectrum of the PC particles (A) of Reference example 1 are shown in FIG. 5. The PSTMAS spectrum selectively captures a spectrum of free moving molecular chains; this method is widely used for analysis of modifying chains on the particle surface. In FIG. 5, a spectrum due to carbons in the phosphorylcholine group is observed at 54.2 ppm.

Figure 6:
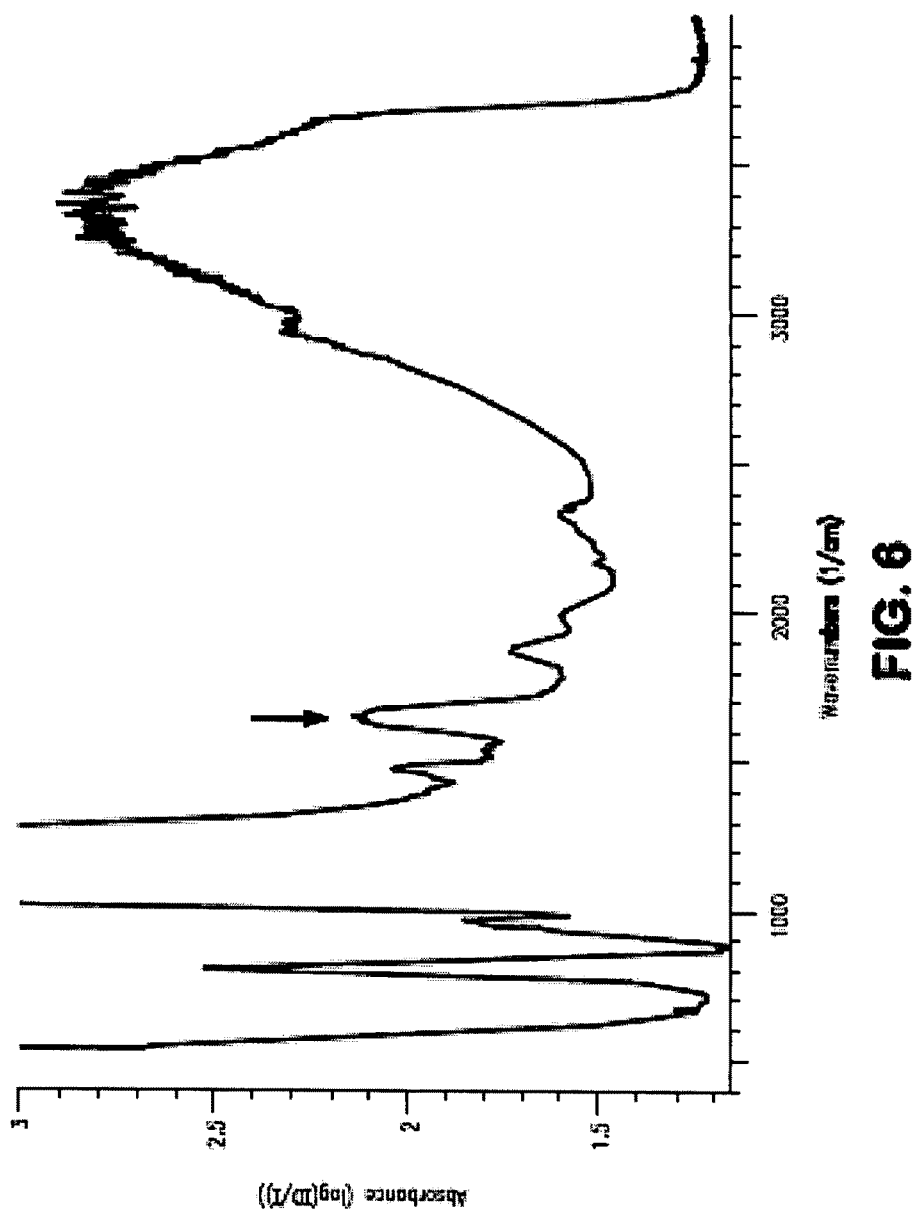
FIG. 6 is a FT-IR spectrum of the PC particles (A) prepared in Reference example 1.

In the 31P-CPMAS spectrum of the PC particles (A) of Reference example 1 in FIG. 6, peaks are detected at almost the same chemical shifts as NaH$_2$PO$_4$, which is measured as a control; this verifies the presence of phosphate groups. The results shown above indicate that phosphorylcholine groups were introduced onto the carrier silica gel surface.

In FIG. 5, spectra due to propyl groups, the spacer, are observed near 9 ppm and 23 ppm, and spectra due to ethyls in phosphorylcholine are observed near 60 ppm and 69 ppm. What is described above indicates that the structures of formulas (10) and (11) are introduced onto the silica gel without being destroyed.

Figure 7:
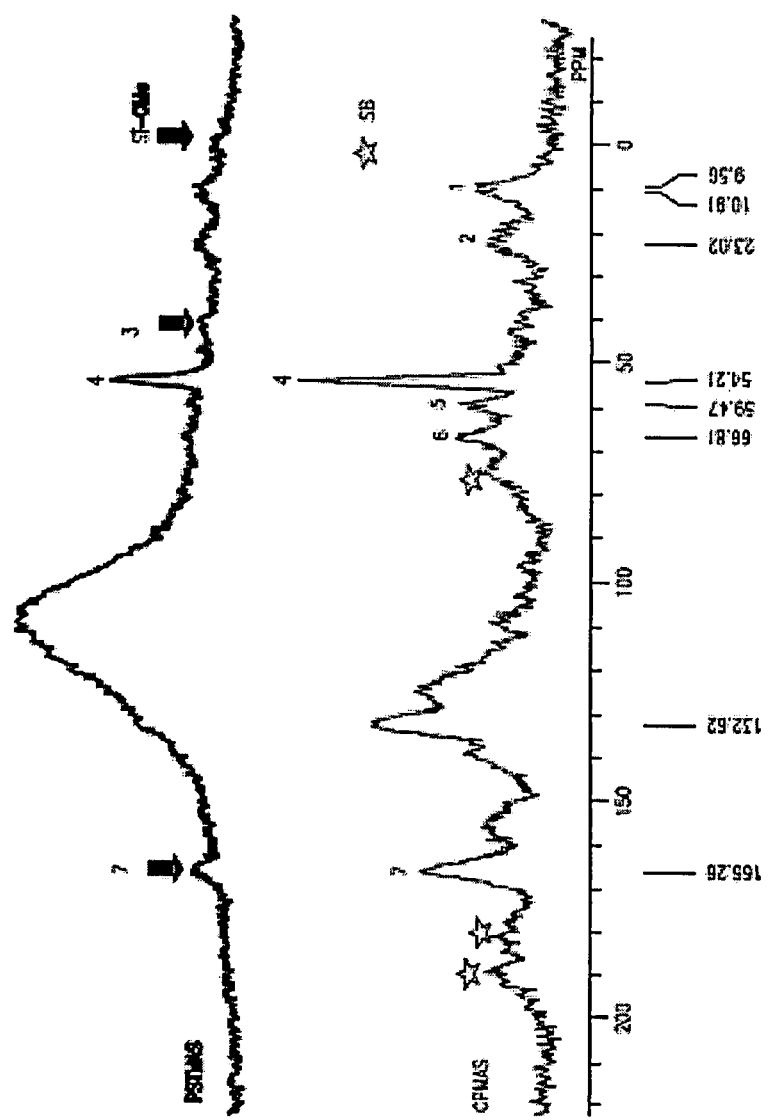
FIG. 7 is a 13C-CPMAS spectrum of the PC particles (A) prepared in Reference example 3.

FIG. 7 shows a FT-IR spectrum of the PC particles (C) of Reference example 3. Absorption specific to amide bonding is observed near 1650 cm$^{-1}$.

"Evaluation of Non-Specific Protein Adsorption on Phosphorylcholine Particles"

Figure 8:
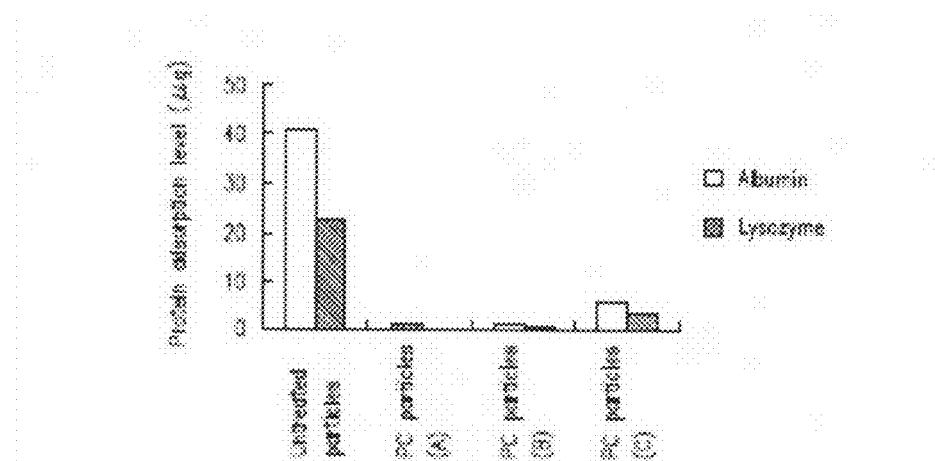
FIG. 8 is an evaluation of suppression of non-specific adsorption of proteins on the PC particles (A), (B), and (C) prepared in Reference example 1, 2, and 3.

25 mg each of untreated silica gel particles having no phosphorylcholine group introduced used in Reference example 1 (abbreviated as "untreated particles") and the PC particles (A), (B), and (C) prepared in Reference examples 1, 2, and 3 were sampled, to each of which 1 ml of distilled water was added, followed by one minute of ultrasonic treatment. After removing the distilled water by means of centrifugation, 1 ml of albumin (100 µg/ml) or lysozyme (100 µg/ml) was added, followed by a 1 hour reaction at room temperature and cleaning by means of centrifugation/purification (5,000 g) 5 times with PBS. 1 ml of SDS (1%) was then added, followed by a 1 hour reaction at room temperature and centrifugation (5,000 g); the supernatant was quantified with the Micro BCA method. The results are shown in FIG. 8. PC particles (A), which had been treated with phosphorylcholine groups, showed significantly suppressed adsorption of both albumin and lysozyme compared with the agarose particles. PC particles (B) and (C) showed even more suppressed adsorption of both albumin and lysozyme compared with untreated particles or PC particles (A).

Example 1

"Affinity Particles (Af Particles (A)) that are Inorganic Particles Having Phosphorylcholine Groups and Amino Groups Covalently Bonded onto their Surface"

87.9 µl of a methanol solution containing 45 µmol of the compound of formula (10) prepared in Synthesis example 3 and 50 µl of a methanol solution containing 5 µmol of 3-aminotrimethoxysilane were sampled, to which 47.5 ml of methanol and 2.5 ml of distilled water were added, and then 5 g of silica gel having an average particle size of 1.5 µm and a specific surface area of 6 m$^2$/g was added. This particle dispersion was refluxed at 80° C. overnight for coupling. After the refluxing, the particles were cleaned by means of centrifugation using methanol to obtain the Af particles of claim 1 (hereafter "Af particles (A)"). FIG. 4 shows the P quantification measurements of the Af particles (A) prepared in the aforementioned procedure using the surface modifier of Synthetic example 3. The PC introduction level thus determined was 2.7 µmol/g-particles, which confirmed the introduction of PC groups onto the particle surface.

Example 2

"Affinity Particles (Af Particles (B)) that are Inorganic Particles Having Phosphorylcholine Groups and Amino Groups Covalently Bonded onto their Surface"

250 µl of a dimethylformamide solution containing 45 µmol of the compound of formula (11) prepared in Synthesis example 4 and 50 µl of a dimethylformamide solution containing 5 µmol of 3-aminotrimethoxysilane were sampled, to which 5 g of silica gel having an average particle size of 1.5 µm and a specific surface area of 6 m$^2$/g was added. This particle dispersion was refluxed at 160° C. overnight for coupling. After the refluxing, the particles were cleaned by means of centrifugation using methanol to obtain the affinity particles of claim 1 (hereafter "Af particles (B)"). FIG. 4 shows the P quantification measurements of the Af particles (B) prepared in the aforementioned procedure using the surface modifier of Synthetic example 4. The PC introduction level thus determined was 3.3 µmol/g-particles, which confirmed the introduction of PC groups onto the particle surface.

Example 3

"Affinity Particles (Af Particles (C)) that are Inorganic Particles Having Phosphorylcholine Groups and Amino Groups Covalently Bonded onto their Surface"

250 µl of a methanol solution containing 45 µmol of the compound of formula (11) prepared in Synthesis example 4 and 50 µl of a dimethylformamide solution containing 5 µmol of 3-aminotrimethoxysilane were sampled, to which 47.5 ml of dimethylformamide and 2.5 ml of distilled water were added, and then 5 g of silica gel having an average particle size of 1.5 µm and a specific surface area of 6 m$^2$/g was added. This particle dispersion was refluxed at 160° C. overnight for coupling. After the refluxing, the particles were cleaned by means of centrifugation using methanol to obtain the affinity particles of claim 1 (hereafter "Af particles (C)"). FIG. 4 shows the P quantification measurements of the Af particles (C) prepared in the aforementioned procedure using the surface modifier of Synthetic example 4. The PC introduction level thus determined was 6.3 μmol/g-particles, which confirmed the introduction of PC groups onto the particle surface.
"Evaluation of the Selectivity of Affinity Particles, Part 1"

Figure 9:
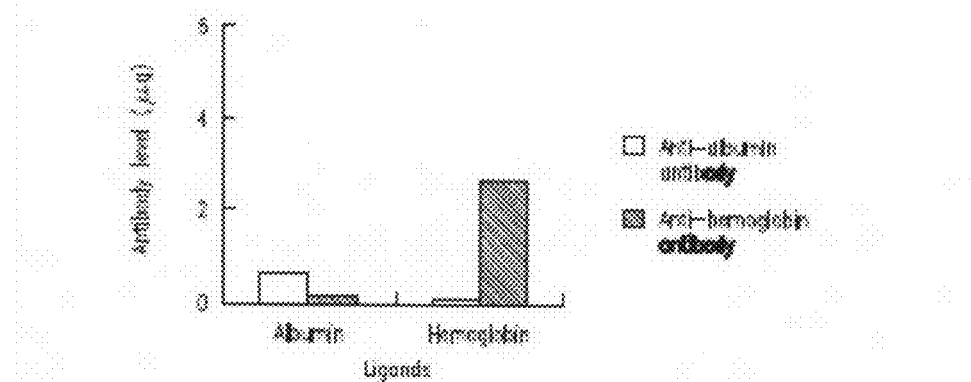
FIG. 9 is a selectivity evaluation of the Af particles (A) on the anti-bovine albumin antibody and anti-human hemoglobin antibody that was conducted in Example 1.
Figure 10:
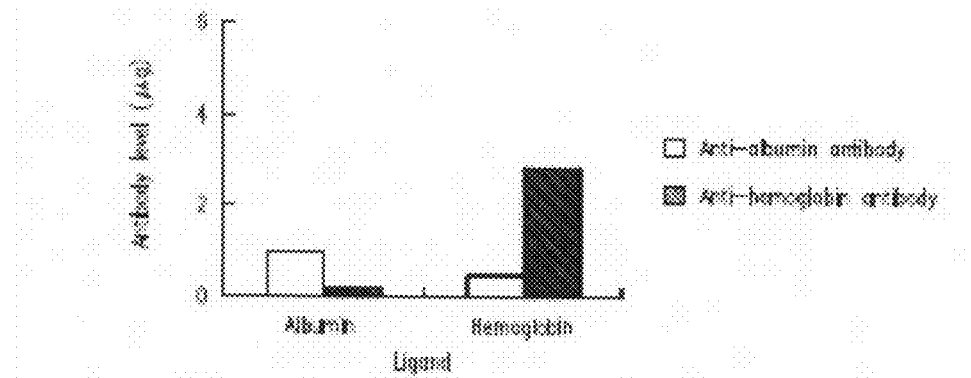
FIG. 10 is a selectivity evaluation of the Af particles (B) on the anti-bovine albumin antibody and anti-human hemoglobin antibody that was conducted in Example 2.
Figure 11:
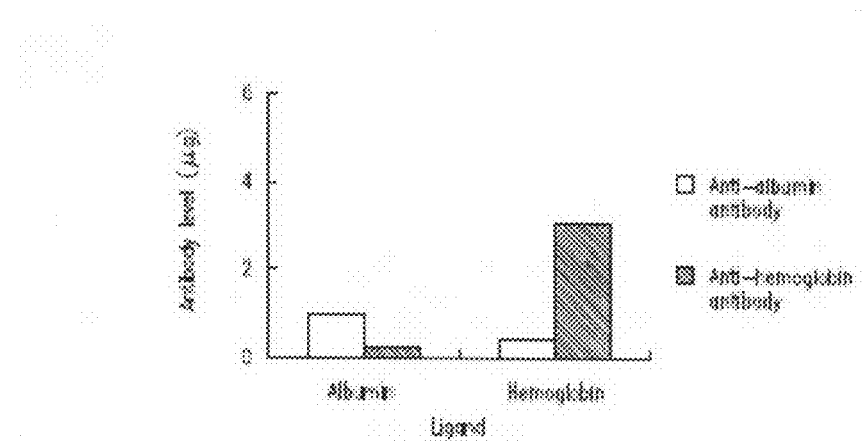
FIG. 11 is a selectivity evaluation of the Af particles (C) on the anti-bovine albumin antibody and anti-human hemoglobin antibody that was conducted in Example 3.

Next, the affinity separation method shown in claim 6 is described. 25 mg each of Af particles (A), (B), and (C) prepared in Examples 1, 2, and 3 were sampled, to each of which 1 ml of distilled water was added, followed by one minute of ultrasonic treatment. After removing the distilled water by means of centrifugation, 1 ml of a glutaraldehyde solution (8%) and 10 mg of sodium cyanotrihydroborate, for stabilizing the Schiff base, were added to these affinity particles and the reaction was carried out for 5 hours at room temperature, followed by a centrifugation/purification (5,000 g) operation 5 times using MQ water for cleaning. The affinity particles of claim 2 that have glutaraldehyde as reactive groups or adsorptive groups to which the ligand can bind were thus obtained. 1 ml of bovine albumin (1 mg/ml) or human hemoglobin (1 mg/ml) and 10 mg of sodium trihydroborate were added and the reaction was carried out for 1 day at room temperature, followed by 4 times of a centrifugation/purification (5,000 g) with PBS. This bovine albumin or human hemoglobin is the ligand. After this is the affinity separation method shown in claim 7. 1 ml of ethanolamine hydrochloride (0.5 M, pH 7.1) and 10 mg of sodium trihydroborate were added and the reaction was carried out for 1 hour at room temperature to deactivate the remaining glutaraldehyde, followed by 4 times of a centrifugation/purification (5,000 g) with PBS to obtain the affinity particles of claim 3. 1 ml of HRP-conjugated anti-bovine albumin antibody (10 μg/ml) or HRP-conjugated human hemoglobin antibody (10 μg/ml) was added and the reaction was carried out for 1 hour at room temperature, followed by 5 times of a centrifugation/purification (5,000 g) with PBS. An additional 1 ml of PBS was added, followed by stirring; 10 μl each was transferred onto a 96-well plate and a color development test was conducted using substrate TMBZ; the measurement was done at 450 nm. The results are shown in FIG. 9, FIG. 10, and FIG. 11. Af particles (A) exhibited selectivity for human hemoglobin-HRP conjugated anti-human hemoglobin antibody. Also, Af particles (B) and Af particles (C) exhibited selectivity for both bovine albumin-HRP conjugated anti-bovine albumin antibody and human hemoglobin-HRP conjugated anti-human hemoglobin antibody.

"Evaluation of the Selectivity of Affinity Particles, Part 2"

Goat anti-serum for human hemoglobin was used to conduct a selectivity test. 25 mg each of Af particles (A) and (C) prepared in Examples 1 and 3 were sampled, to each of which 1 ml of distilled water was added, followed by one minute of ultrasonic treatment. After removing the distilled water by means of centrifugation, 1 ml of a glutaraldehyde solution (8%) and 10 mg of sodium cyanotrihydroborate, for stabilizing the Schiff base, were added to these affinity particles and the reaction was carried out for 5 hours at room temperature, followed by a centrifugation/purification (5,000 g) operation 5 times using MQ water for cleaning. The affinity particles of claim 2 that have glutaraldehyde as reactive groups or adsorptive groups to which the ligand can bind were thus obtained. 1 ml human hemoglobin (1 mg/ml) and 10 mg of sodium trihydroborate were added and the reaction was carried out for 1 day at room temperature, followed by centrifugation/purification (5,000 g) 4 times with PBS. This human hemoglobin is the ligand. After this is the affinity separation method shown in claim 7. 1 ml of ethanolamine hydrochloride (0.5 M, pH 7.1) and 10 mg of sodium trihydroborate were added and the reaction was carried out for 1 hour at room temperature to deactivate the remaining glutaraldehyde, followed by a centrifugation/purification (5,000 g) 4 times with PBS to obtain the affinity particles of claim 3. 1 ml of goat anti-serum, diluted 100 times, was then added, followed by a one hour reaction at room temperature. Centrifugation (5,000 g) was then conducted and the supernatant was sampled (supernatant fraction).

Figure 12:
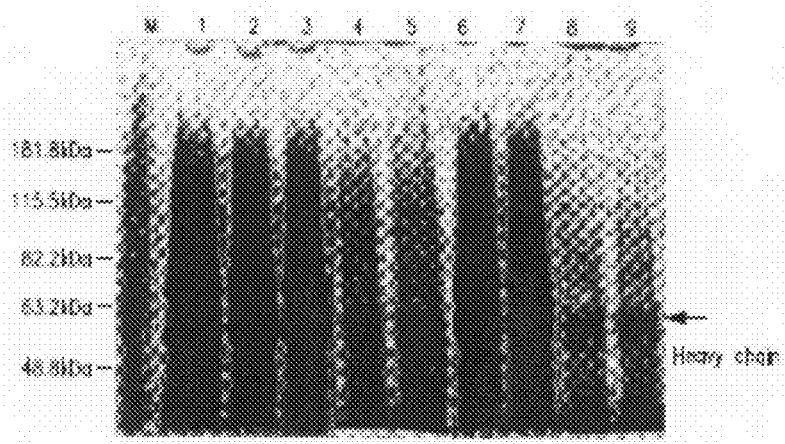
FIG. 12 is a selectivity evaluation of the Af particles (A) and (C) on goat anti-serum that was conducted in Examples 1 and 3.

Centrifugation/purification (5,000 g) was conducted 5 times using PBS. 1 ml of a Gly-HCl buffer (0.2M, pH 2.5) was then added and the reaction was carried out for one hour at room temperature to elute the anti-human hemoglobin antibody and centrifugation (5,000 g) was conducted to obtain the supernatant (elution fraction). This supernatant fraction and elution fraction were fed to SDS-PAGE, followed by silver staining; the results are shown in FIG. 12. Both Af particles (A) and (C) exhibit a dark band of the heavy chain of the antibody but no other bands in the elution fraction, which indicates that the antibody was captured highly selectively.

"Evaluation of the Selectivity of Affinity Particles, Part 3"

The goat anti-serum mixed with anti-human hemoglobin was used to conduct a selectivity test. 25 mg each of Af particles (A) and (C) prepared in Examples 1 and 3 were sampled, to each of which 1 ml of distilled water was added, followed by one minute of ultrasonic treatment. After removing distilled water by means of centrifugation, 1 ml of a glutaraldehyde solution (8%) and 10 mg of sodium cyanotrihydroborate, for stabilizing the Schiff base, were added to these affinity particles and the reaction was carried out for 5 hours at room temperature, followed by a centrifugation/purification (5,000 g) operation 5 times using MQ water for cleaning. The affinity particles of claim 2 that have glutaraldehyde as reactive groups or adsorptive groups to which the ligand can bind were thus obtained. 1 ml human hemoglobin (1 mg/ml) and 10 mg of sodium trihydroborate were added and the reaction was carried out for 1 day at room temperature, followed by a centrifugation/purification (5,000 g) 4 times with PBS. This human hemoglobin is the ligand. After this is the affinity separation method shown in claim 7. 1 ml of ethanolamine hydrochloride (0.5 M, pH 7.1) and 10 mg of sodium trihydroborate were added and the reaction was carried out for 1 hour at room temperature to deactivate the remaining glutaraldehyde, followed by a centrifugation/purification (5,000 g) 4 times with PBS to obtain the affinity particles of claim 3. 1 ml of goat anti-serum, diluted 100 times and mixed with 50 μg of anti-human hemoglobin, was then added, followed by a one hour reaction at room temperature. Centrifugation (5,000 g) was then conducted and the supernatant was sampled (supernatant fraction).

Figure 13:
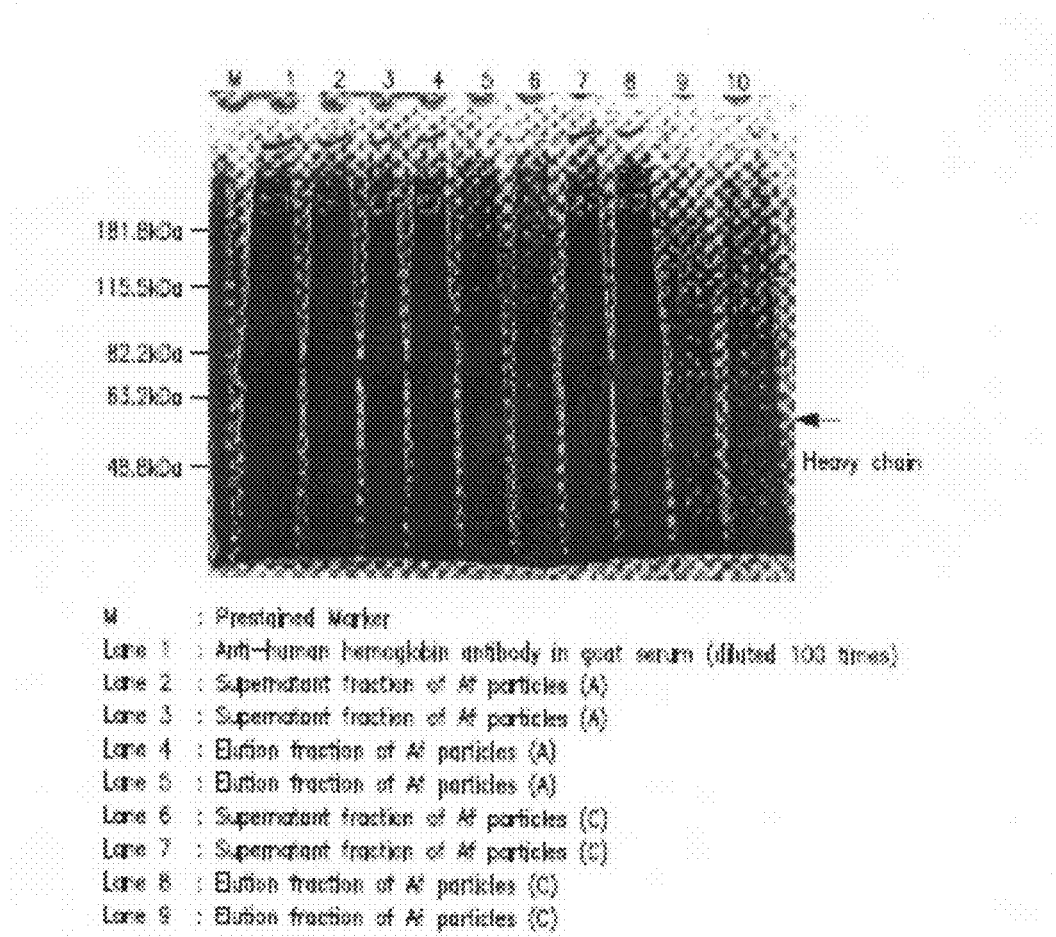
FIG. 13 is a selectivity evaluation of the Af particles (A) and (C) on anti-human hemoglobin in goat serum that was conducted in Examples 1 and 3.

Centrifugation/purification (5,000 g) was conducted 5 times using PBS. 1 ml of a Gly-HCl buffer (0.2M, pH 2.5) was then added and the reaction was carried out for one hour at room temperature to elute the anti-human hemoglobin antibody and centrifugation (5,000 g) was conducted to obtain the supernatant (elution fraction). This supernatant fraction and elution fraction were fed to SDS-PAGE, followed by silver staining; the results are shown in FIG. 13. Both Af particles (A) and (C) exhibit a dark band of the heavy chain of the antibody but no other bands are faint, which indicates that the antibody was captured highly selectively. The band darkness indicates that the antibody capture level is 10-20 μg. The antibody activity of the elution fractions were confirmed by means of sandwich ELISA; the activity was equivalent to 13 μg for Af particles (A) and 10.1 μg for Af particles (C).

Comparative Example 1

"Affinity Particles (Amino Particles) that are Inorganic Particles Having Amino Groups Covalently Bonded onto their Surface"

Figure 14:
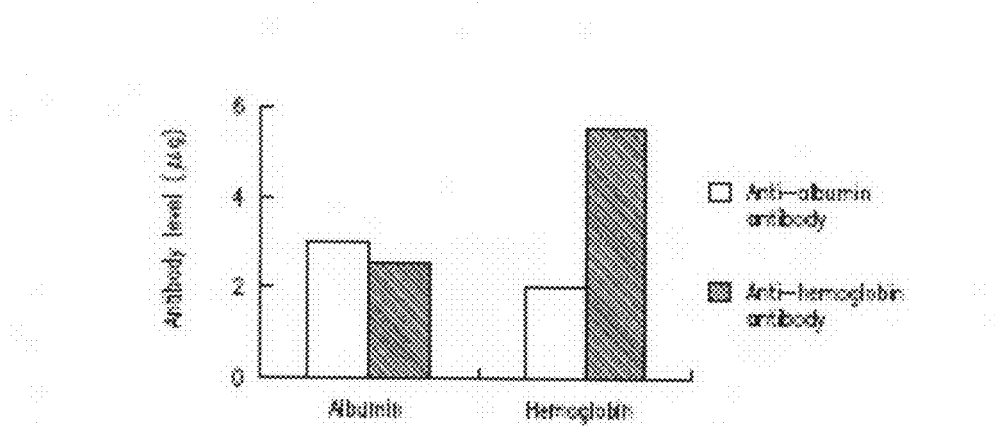
FIG. 14 is a selectivity evaluation of the Af particles (A) on the anti-bovine albumin antibody and anti-human hemoglobin antibody that was conducted in Comparative example 1.

500 μl of a methanol solution containing 50 μmol of 3-aminopropyltrimethoxysilane was sampled, to which 47.5 ml of methanol and 2.5 ml of distilled water were added, and then 5 g of silica gel having an average particle size of 1.5 μm and a specific surface area of 6 m$^2$/g was added. This particle dispersion was refluxed at 80° C. overnight for coupling. After refluxing and then cleaning by means of centrifugation using methanol, the amino particles were obtained. 1 ml of distilled water was added to 25 mg of these amino particles, followed by one minute of ultrasonic treatment. After removing distilled water by means of centrifugation, 1 ml of a glutaraldehyde solution (8%) and 10 mg of sodium cyanotrihydroborate, for stabilizing the Schiff base, were added to these affinity particles and the reaction was carried out for 5 hours at room temperature, followed by a centrifugation/purification (5,000 g) operation 5 times using MQ water for cleaning. Glutaraldehyde is the reactive group or adsorptive group that can bind to the ligand. 1 ml of bovine albumin (1 mg/ml) or human hemoglobin (1 mg/ml) and 10 mg of sodium trihydroborate were added and the reaction was carried out for 1 day at room temperature, followed by centrifugation/purification (5,000 g) 4 times with PBS. This bovine albumin or human hemoglobin is the ligand. 1 ml of ethanolamine hydrochloride (0.5 M, pH 7.1) and 10 mg of sodium trihydroborate were added and the reaction was carried out for 1 hour at room temperature to deactivate the remaining glutaraldehyde, followed by centrifugation/purification (5,000 g) 4 times with PBS to obtain the affinity particles of claim 3. 1 ml of HRP-conjugated anti-bovine albumin antibody (10 μg/ml) or HRP-conjugated human hemoglobin antibody (10 μg/ml) was added and the reaction was carried out for 1 hour at room temperature, followed by centrifugation/purification (5,000 g) 5 times with PBS. An additional 1 ml of PBS was added, followed by stirring; 10 μl each was transferred onto a 96-well plate and a color development test was conducted using substrate TMBZ; the measurement was done at 450 nm. The results are shown in FIG. 14. There is a high level of non-specific adsorption of proteins and the selectivity is low.

Industrial Applicability

The affinity particles of the present invention capture only the target protein that is desired to be separated and therefore they exhibit very high selectivity. They also exhibit superior dispersion properties and make separation from liquid samples very easy. Since a target substance can be separated easily with high accuracy using affinity particles made from inexpensive inorganic particles, the present invention is useful in bio-industries where a highly accurate separation and detection of the target substance is required.

The invention claimed is:

1. Affinity particles capable of bonding with ligands comprising:
   (a) inorganic particles comprised of one or more of silica, titanium oxide, zinc flower, alumina, iron oxide, talc, mica, sericite, and gold colloid particles;
   (b) reactive or adsorptive groups bound to the surface of the inorganic particles, said reactive or adsorptive groups capable of bonding with ligands; and
   (c) phosphorylcholine groups represented by the following formula (1):

[Chemical formula 1]

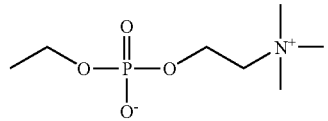

covalently bonded onto the surface of the inorganic particles, wherein said ligands are selected from the group consisting of antibodies, antigens, enzymes, substrates, receptors, lectin, peptides, DNA, RNA, aptamers, protein A, protein G, avidin, biotin, chelating compounds, and metal ions.

2. The affinity particles of claim 1, wherein said inorganic particles are silica having an average particle size of 20 nm to 500 μm, and a specific gravity of 1.0 g/cm$^3$ or higher.

3. Affinity particles having ligands bound to the surface thereof, said affinity particles comprising:
   (a) inorganic particles comprised of one or more of silica, titanium oxide, zinc flower, alumina, iron oxide, talc, mica, sericite, and gold colloid particles;
   (b) one or more ligands are covalently bound or adsorbed to the surface of the inorganic particles via reactive or adsorptive groups; and
   (c) phosphorylcholine groups represented by the following chemical formula 3:

[Chemical formula 3]

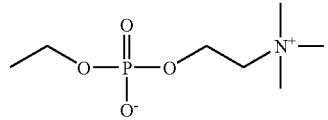

covalently bonded onto the surface of said inorganic particles; and wherein the ligands have specific affinity with a certain target substance, and are selected from the group consisting of antibodies, antigens, enzymes, substrates, receptors, lectin, peptides, DNA, RNA, aptamers, protein A, protein G, avidin, biotin, chelating compounds, and metal ions.

4. The affinity particles of claim 3, wherein said inorganic particles are silica having an average particle size of 20 nm to 500 μm, and a specific gravity of 1.0 g/cm$^3$ or higher.

* * * * *